(12) United States Patent
Ihalainen et al.

(10) Patent No.: US 6,732,988 B2
(45) Date of Patent: May 11, 2004

(54) ARTICULATED ARM SYSTEM FOR SUPPORTING MEDICAL IMAGING DEVICES

(75) Inventors: Pekka Ihalainen, Tuusula (FI); Jukka Salminen, Helsinki (FI)

(73) Assignee: Instrumentarium Corp., Tuusula (FI)

( * ) Notice: Subject to any disclaimer, the term of this patent is extended or adjusted under 35 U.S.C. 154(b) by 0 days.

(21) Appl. No.: 10/148,278

(22) PCT Filed: Nov. 30, 2000

(86) PCT No.: PCT/FI00/01045

§ 371 (c)(1),
(2), (4) Date: May 28, 2002

(87) PCT Pub. No.: WO01/40700

PCT Pub. Date: Jun. 7, 2001

(65) Prior Publication Data

US 2003/0001056 A1 Jan. 2, 2003

(30) Foreign Application Priority Data

Dec. 1, 1999 (FI) .............................................. 19992570

(51) Int. Cl.⁷ ................................................. E04G 3/00
(52) U.S. Cl. ............................... 248/276.1; 248/280.11; 248/281.11; 248/292.13
(58) Field of Search ........................ 248/276.1, 280.11, 248/281.11, 284.1, 292.12, 292.13

(56) References Cited

U.S. PATENT DOCUMENTS

| 8,723 | A | * | 2/1852 | Starr ............................. 4/599 |
| 2,941,776 | A | * | 6/1960 | Lauterbach ............ 248/280.11 |
| 3,000,606 | A | * | 9/1961 | Storm, Jr. et al. ...... 248/280.11 |
| 3,160,379 | A | * | 12/1964 | Gardella .................. 248/125.7 |
| 4,080,530 | A | * | 3/1978 | Krogsrud .................... 362/402 |
| 4,160,536 | A | | 7/1979 | Krogsrud |
| 4,318,538 | A | | 3/1982 | Janssen |
| 4,427,382 | A | * | 1/1984 | Hoffmeister et al. .......... 433/79 |
| 4,501,557 | A | | 2/1985 | Tamura et al. |
| 4,657,217 | A | * | 4/1987 | Kiesel et al. .......... 248/123.11 |
| 4,682,749 | A | * | 7/1987 | Strater ..................... 248/284.1 |
| 5,213,293 | A | * | 5/1993 | Muentener et al. ..... 248/123.11 |
| 5,299,288 | A | | 3/1994 | Glassman et al. |
| 6,082,552 | A | * | 7/2000 | Pollock et al. ................. 211/18 |
| 6,105,909 | A | * | 8/2000 | Wirth et al. ............. 248/123.2 |
| 6,523,796 | B2 | * | 2/2003 | Wirth et al. ............. 248/284.1 |

FOREIGN PATENT DOCUMENTS

| DE | 2659444 B1 | * | 1/1978 |
| DE | 2654334 A1 | * | 6/1978 |
| DE | 195 01 028 | | 7/1996 |
| EP | 185229 | | 6/1986 |
| EP | 631088 | | 12/1994 |
| EP | 851259 | | 7/1998 |
| FI | 67257 | | 10/1984 |
| FI | 103177 | | 5/1999 |

* cited by examiner

Primary Examiner—Anita King
Assistant Examiner—Naschica S. Morrison
(74) Attorney, Agent, or Firm—Andrus, Sceales, Starke & Sawall, LLP

(57) ABSTRACT

The invention relates to an articulated arm system (20) for attaching different medical imaging devices (11) to support structures (14) in an articulated manner. The articulated arm comprises at least one parallelogram device (15a, 15b) including a counterbalancing mechanism for holding the articulated arm and the device (11) supported by it in place when the device is located in the desired imaging position. The system further comprises braking and/or locking means (2: 22) which act on at least one strut bar (6, 7) of the said at least one parallelogram device (15a, 15b) and/or on the at least one additional strut bar (1) in order to prevent mutual linear movement of the strut bars (6, 7) of the parallelogram device, and which braking and/or locking means comprise actuators (3–5; 23; 24).

7 Claims, 7 Drawing Sheets

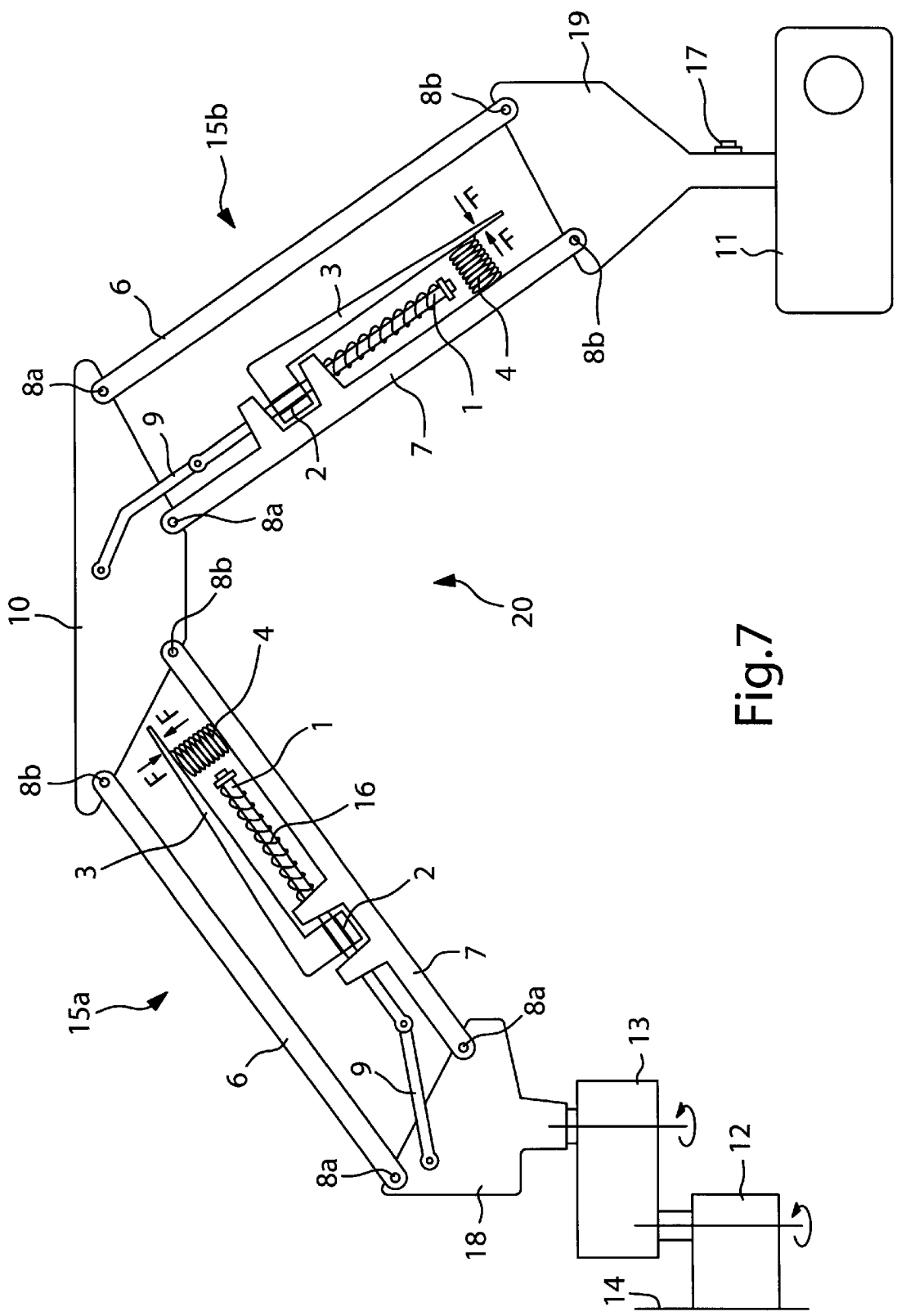

ARTICULATED ARM SYSTEM FOR SUPPORTING MEDICAL IMAGING DEVICES

CROSS REFERENCE TO RELATED APPLICATION

The present application is the U.S. national stage application of International Application PCT/FI00/01045, filed Nov. 30, 2000, which international application was published on as International Publication WO 01/40700. The International Application claims priority of Finnish Patent Application 19992570, filed Dec. 1, 1999.

The present invention relates to an articulated arm system for attaching different medical imaging devices to support structures in an articulated manner, the articulated arm comprising at least one parallelogram device with at least two mutually parallel strut bars; and a counterbalancing mechanism for holding the articulated arm and the device supported by it in place when the device is located in the desired imaging position. The counterbalancing mechanism preferably comprises at least one additional strut bar and counterbalancing means.

There are already articulated arm systems of the type mentioned in the introduction on the market, one problem with which is, however, the loosening of the springs and articulations with time, due to which the device will not, for example, remain in place during imaging, whereby the imaging result will obviously deteriorate. Accordingly, one important object of the present invention is to provide an improved articulated arm system for attaching different medical imaging devices, for example, devices for imaging the head area, such as intraoral and panoramic imaging devices, to support structures in an articulated manner, by means of which articulated arm system is ensured, through relatively simple measures, that the device will stay in place during imaging.

BRIEF SUMMARY OF THE INVENTION

In order to achieve the objects of the invention, the articulated arm system according to the first aspect of the invention for attaching different medical imaging devices to support structures in an articulated manner, the articulated arm comprising at least one parallelogram device with at least two mutually parallel strut bars; and a counterbalancing mechanism for holding the articulated arm and the device supported by it in place when the device is located in the desired imaging position, is characterised in that the system further comprises braking and/or locking means which act on at least one strut bar of the said at least one parallelogram device and/or on the said at least one additional strut bar in order to prevent mutual linear movement of the strut bars of the parallelogram device, and which braking and/or locking means comprise actuators.

An articulated arm system relating to a second aspect of the invention for attaching different medical imaging devices to support structures in an articulated manner, the articulated arm comprising at least one parallelogram device with at least two mutually parallel strut bars; and a counterbalancing mechanism for holding the articulated arm and the device supported by it in place when the device is located in the desired imaging position, is characterised in that the counterbalancing mechanism is comprised of an air spring arranged between one strut bar and an articulated part, which spring can be locked into the desired position, thus preventing the mutual linear movement of the strut bars of the parallelogram device.

BRIEF DESCRIPTION OF THE DRAWING

The invention is described in greater detail in the following, with reference to the appended drawings, in which:

FIGS. 6 and 7 show further alternative embodiments of the articulated arm system.

DETAILED DESCRIPTION OF THE INVENTION

Figure 1:
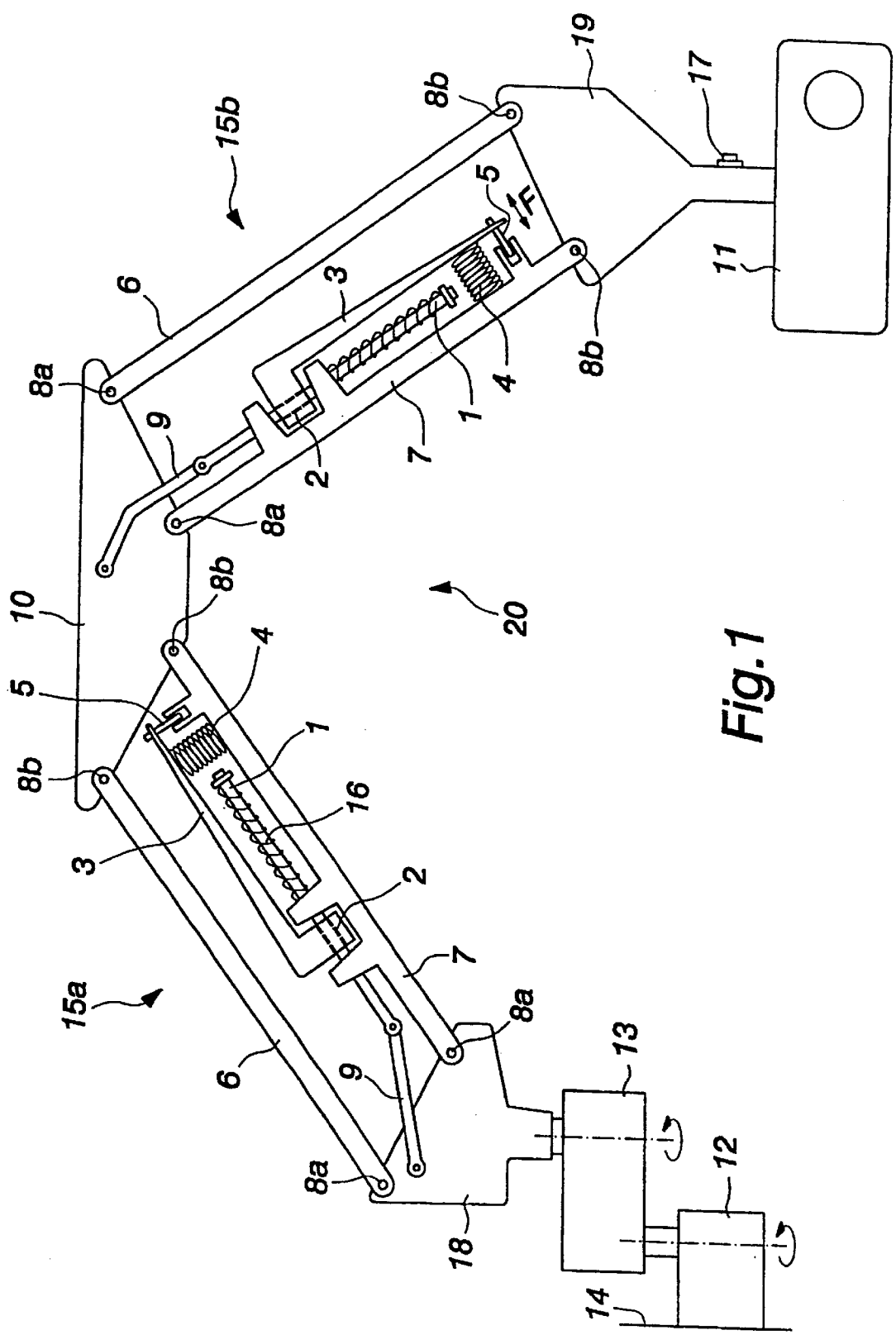
FIG. 1 shows a diagrammatic side view of one embodiment of the articulated arm system relating to the invention.

According to FIG. 1, the articulated arm system 20 comprises a first parallelogram device 15a, a spacing piece 10 and a second parallelogram device 15b. The first parallelogram device 15a is attached through a connecting piece 18 and articulation pieces 13 and 12 to a support structure 14, for example, a wall or a pillar. At the free end of the second parallelogram device 15b is attached the desired imaging device 11, for example, an intraoral imaging device, through a connecting piece 19. Both parallelogram devices 15a, 15b comprise parallel strut bars 6, 7 which are connected to the spacing piece 10 and the connecting pieces 18 and 19 by means of articulations 8a and 8b. The mutual distance between the pivots 8a in the connecting piece 18 of the parallelogram device 15a is equal to the mutual distance between the pivots 8b in the spacing piece 10, and correspondingly, the mutual distance between the pivots 8a in the parallelogram device 15b is equal to the mutual distance between the pivots 8b. This means that when the articulated arm is used for adjusting the device 11 into the correct position, the spacing piece 10 will remain in essentially the same position throughout; in the case shown, the spacing piece 10 is essentially horizontal throughout.

Figure 6:
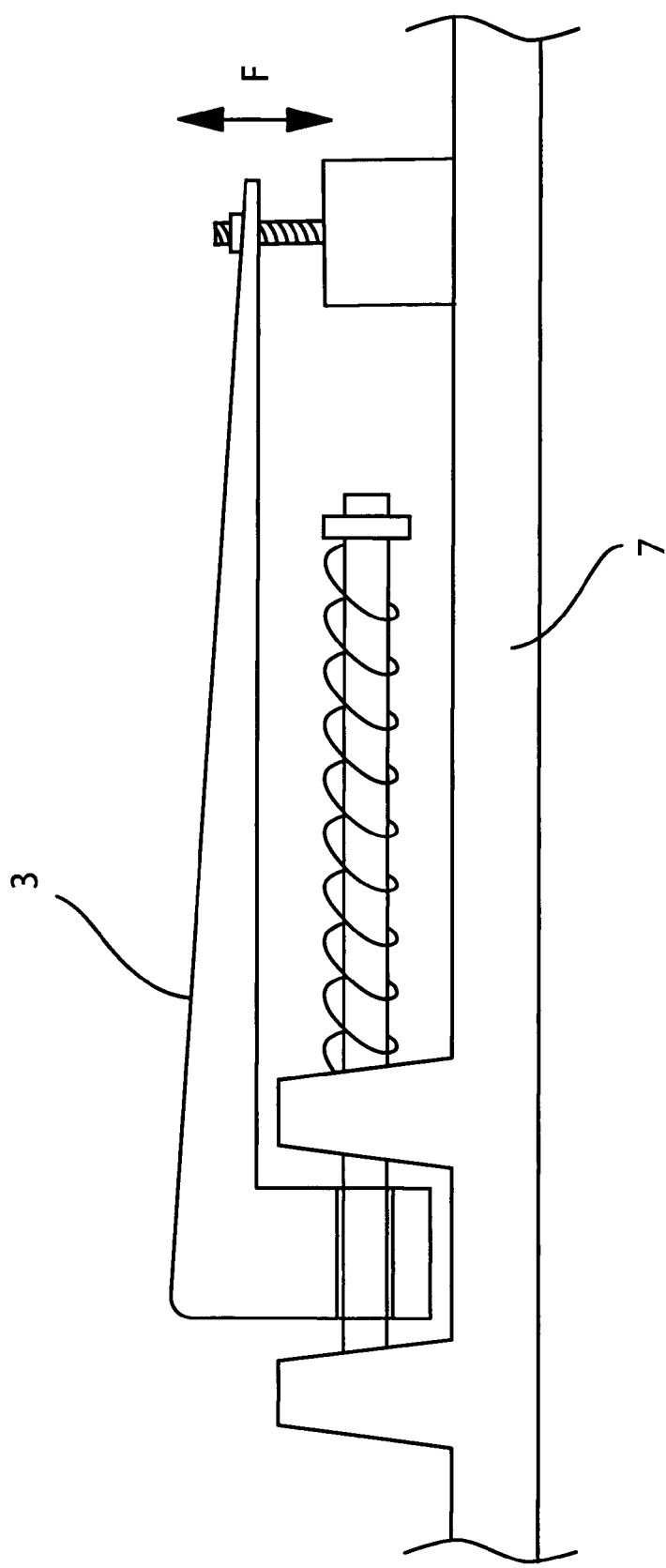

In the embodiment shown in FIG. 1, both parallelogram devices have a counterbalancing mechanism with an additional strut bar 1, around which there is a counterbalancing spring 16 for holding the articulated arm and the device supported by it in place. The additional strut bar 1 is preferably round and, in the embodiment shown, connected with bar 9 in parallelogram device 15a to the connecting piece 18 and in parallelogram device 15b with the spacing piece 10. To prevent unintentional movement of the articulated arm, in the solution relating to the invention, braking and/or locking means have been mounted around the additional strut bar 1. In the embodiment shown, these means comprise a locking piece 2 which includes a sleeve part surrounding the additional strut bar 1. This piece 2 is connected to a lever arm 3 which is loaded by force F to press the sleeve against the additional strut bar 1. In the embodiment shown, the force F is generated by means of the spring 4. In this solution, the locking is normally always on, and in order to adjust the device into the desired position, at the end of the lever arm 3 are arranged actuators 5, for example, a solenoid, which is made to pull by pressing the switch button 17 on the connecting piece 19, whereby the lever arm 3 presses against the force of the spring 4, allowing easy movement of the additional strut bar 1 inside the sleeve part of the locking piece 2. The use of this locking piece 2 can also be implemented vice versa, whereby the lever arm 3 is normally turned in such a way that the additional strut bar 1 is able to move inside the sleeve part, and when the articulated arm is to be locked, for example, a solenoid 5 is used for turning the lever arm 3 in such a way that the sleeve part presses against the additional strut bar 1. Instead of a spring 4 and a solenoid 5, the actuator of the lever arm 3 may be, for example, a motor equipped with a self-locking worm gear (see FIG. 6), or even manual operation (see FIG. 7).

Figure 2:
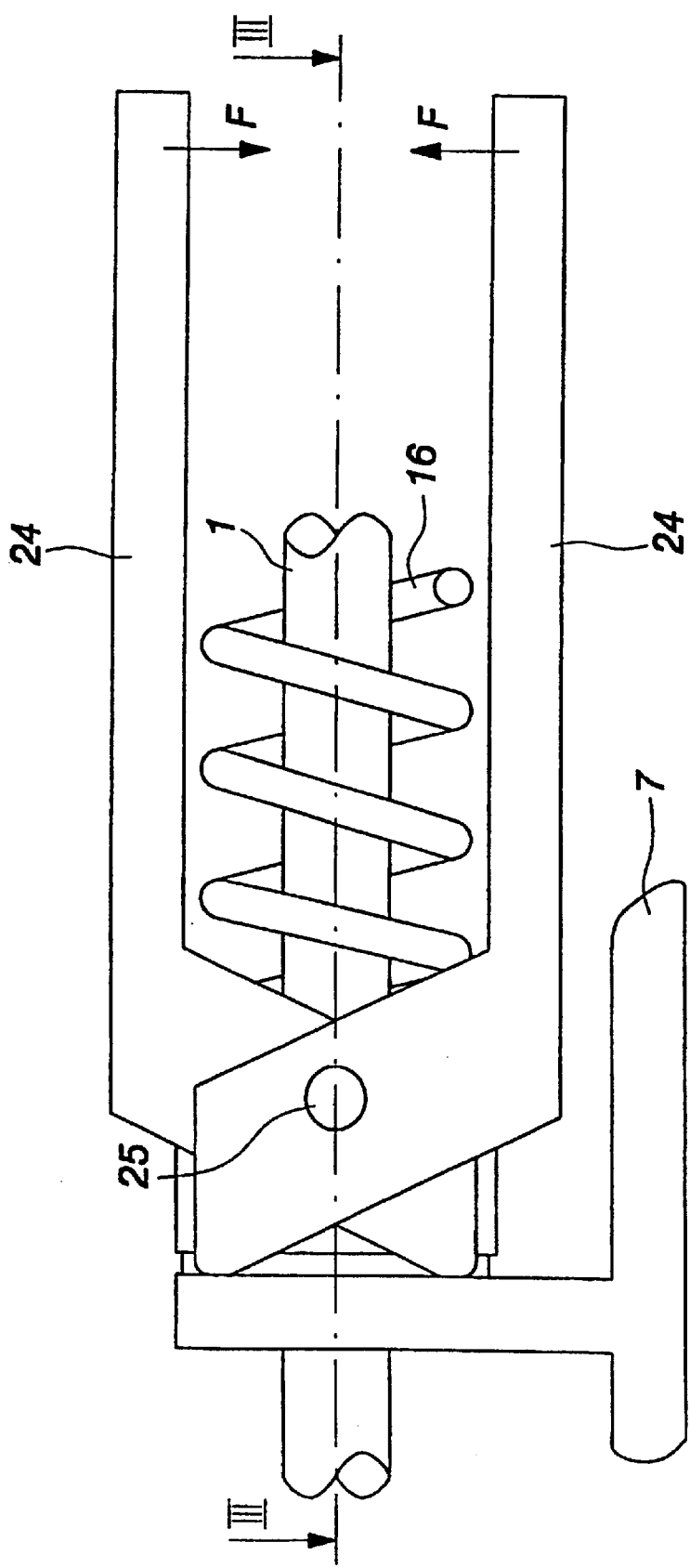
FIG. 2 shows diagrammatically an alternative embodiment of the braking and/or locking means used in the articulated arm system relating to the invention.
Figure 3:
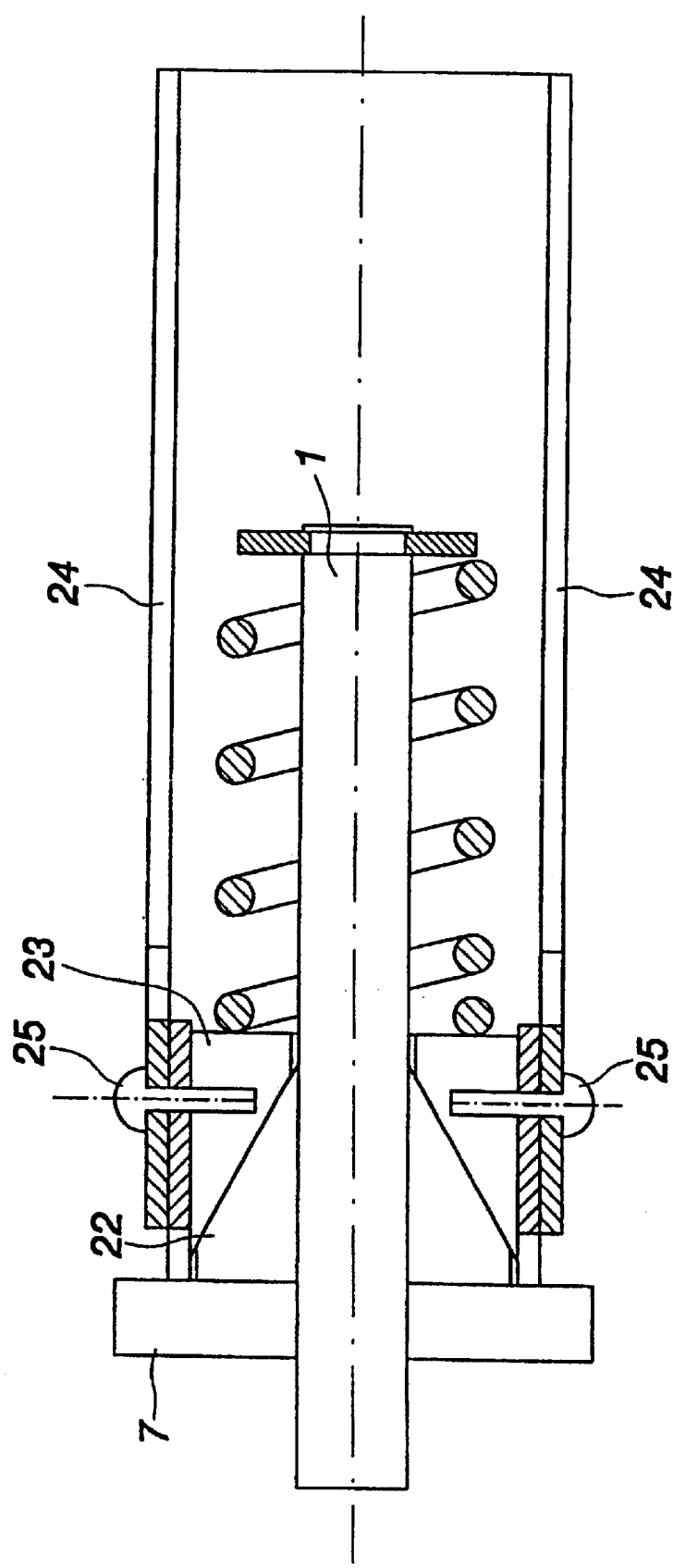
FIG. 3 shows a section along line III—III of the embodiment shown in FIG. 2, FIGS. 4–5 show diagrammatically certain alternative embodiments of the articulated arm system relating to the invention.

FIGS. 2 and 3 show an alternative friction-operated locking and/or braking device acting on the additional strut bar 1, in which device a conical locking piece 22 is used instead of a sleeve, the locking piece being provided with at least one axial gap which allows circumferential movement of the locking piece in such a way that the locking piece is pressed by means of the opposite conical piece 23 loaded by the counterbalancing spring 16 against the surface of the additional strut bar 1. Each gap may extend either over only a part of the axial length of the locking piece or over its entire length, which means that the conical piece may also be comprised of two or more separate parts. To the conical piece 23 are attached lever arms 24 by means of joint pins 25, the lever arms forming a pliers-type means on either side of the additional strut bar 1. By pressing the lever arms 24 which are against each other at each time towards each other, the conical piece 23 is made to move away from the attachment with the locking piece 22, which means that the additional strut bar 1 can move easily with respect to the locking piece 22. When the compression on the lever arms 24 ceases, the spring 16 loads the conical piece 23 back against the locking piece 22. The locking piece 22 may also be made of an elastic material, for example, rubber, and its shape may also be other than conical. The elastic locking piece may extend uniformly around the additional strut bar 1, whereby elasticity will make possible pressing it against the additional strut bar.

Figure 4:
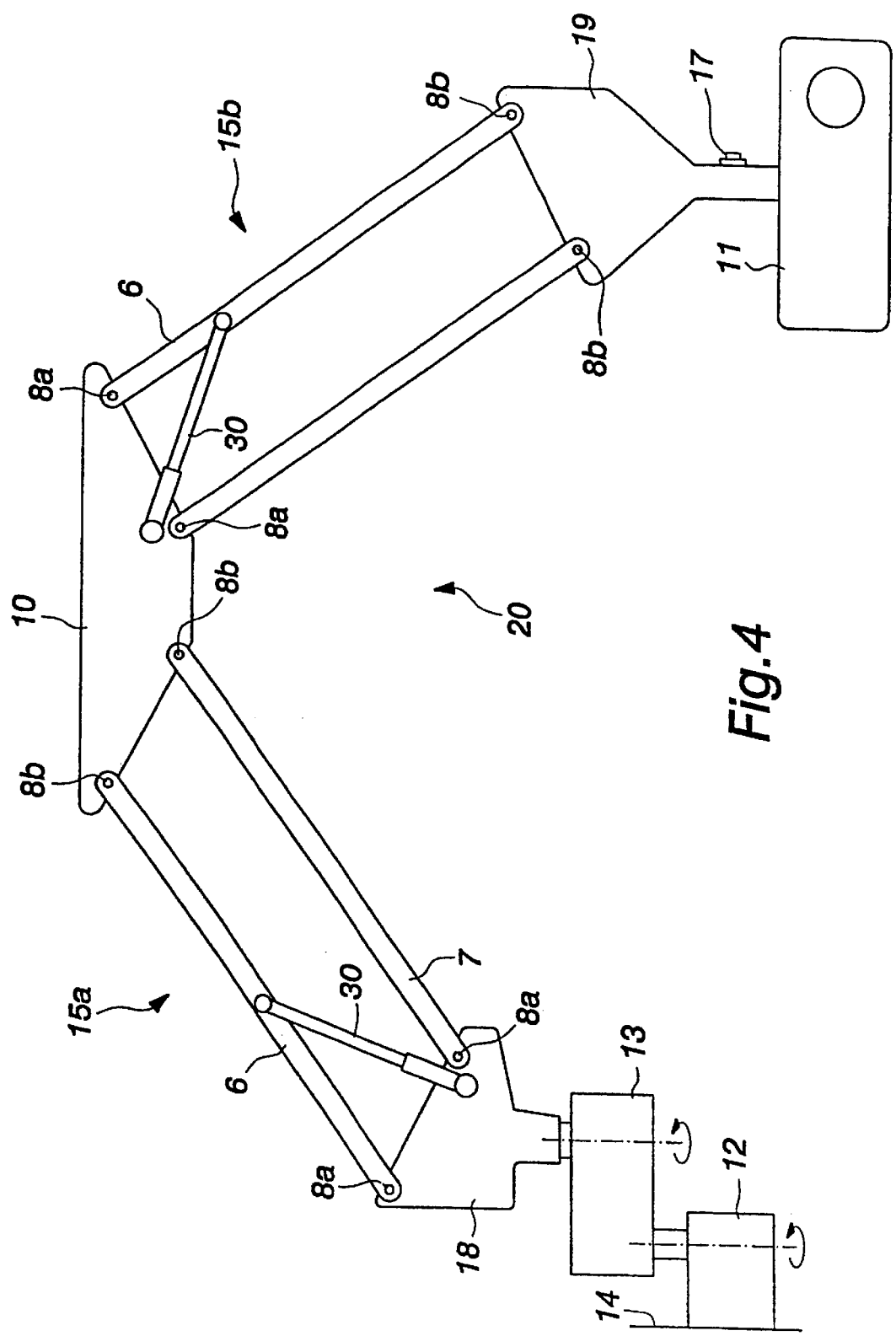

FIG. 4 shows another alternative embodiment in which the counterbalancing mechanism of the parallelogram device is comprised of the lock-up air spring 30 arranged each time between the connecting piece 18 or 19 and the strut bar 6. In this case, the additional strut bar 1 and the counterbalancing spring 16 connected to it can be omitted. Locking the air spring prevents the mutual linear movement of the strut bars 6 and 7 of the parallelogram device 15a and 15b, respectively. The air spring may also be arranged in only one parallelogram device, while the other is equipped with, for example, the counterbalancing mechanism shown in FIG. 1.

Figure 5:
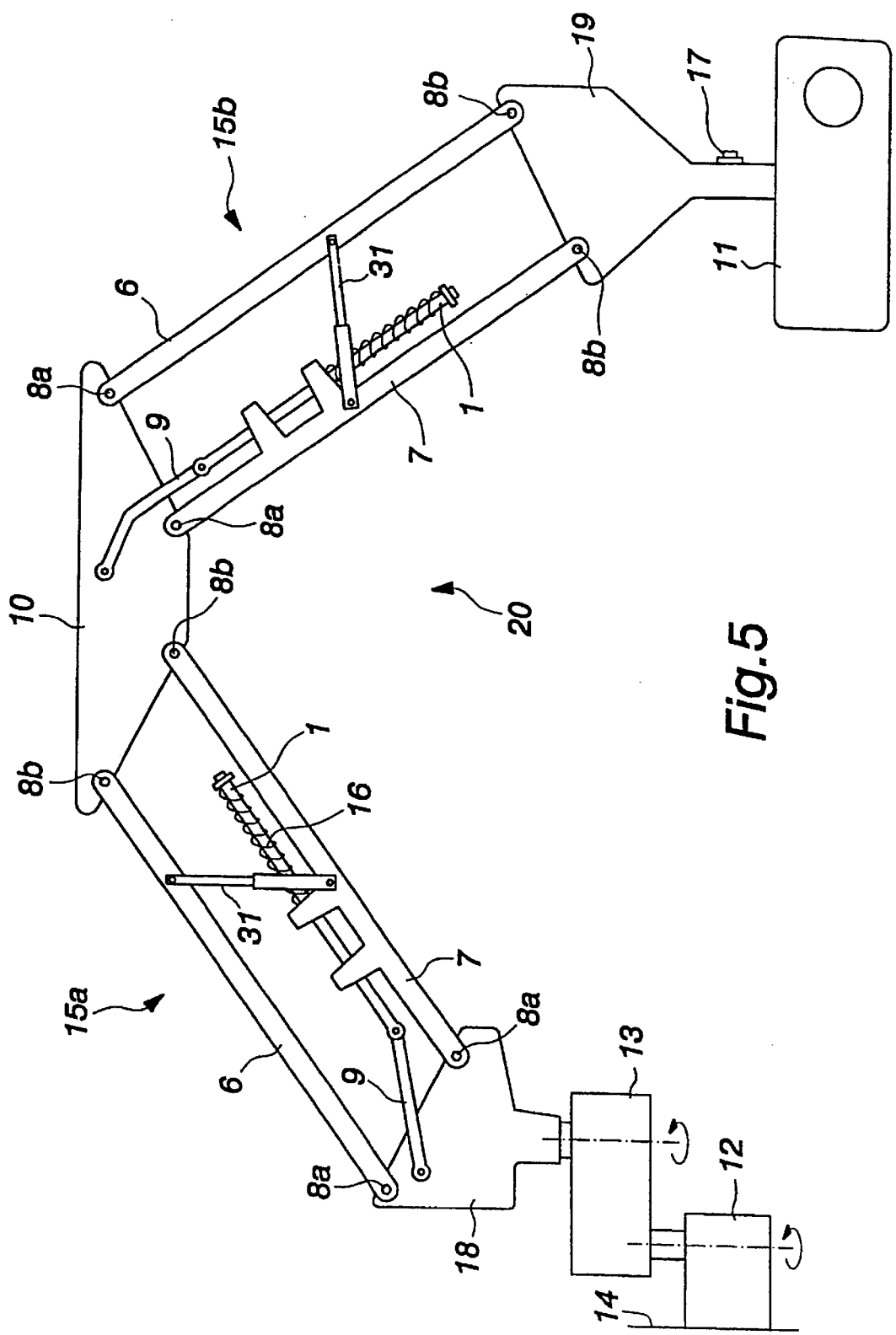

FIG. 5 shows yet another alternative embodiment which differs from the embodiment shown in FIG. 1 in that between the strut bars 6 and 7 of the parallelogram device is arranged a transverse lever 31 by means of which the strut bars 6, 7 can be interlocked, in which case the means 2 to 5 are omitted. The transverse lever may be, for example, a lock-up telescopic lever which allows mutual linear movement of the strut bars when the lever is not locked, for example, a lock-up air spring. As a lever may also be used a rigid lever which is attached at least at one end to the corresponding strut bar 6 or 7 in such a way that the end of the lever can move with respect to the strut bar when not locked, allowing mutual linear movement of the strut bars 6, 7, and when locked, will prevent the mutual linear movement. This attachment of the transverse lever to the strut bar may be realised, for example, by providing the end of the transverse lever with a pin which moves in a guide groove or loop formed in the strut bar.

The embodiments described above are merely examples of certain preferred implementations of the invention and are not intended to limit the scope of protection of the invention defined in the appended claims.

What is claimed is:

1. An articulated arm system (20) for attaching a medical imaging device (11) to a support structure (14) in an articulated manner, the articulated arm system comprising:
   at least one parallelogram device (15a,15b) interposable between the device and the support, said parallelogram device having at least two mutually parallel strut bars (6,7);
   a counterbalancing mechanism for said parallelogram device having at least one additional strut bar (1) and counterbalancing means (16) for holding the articulated arm system and the device (11) supported thereby in place when the device is located in a desired imaging position
   braking and/or locking means for preventing mutual linear movement of the parallel strut bars (6,7) of the parallelogram device, said braking and/or locking means having a locking piece (2) surrounding said additional strut bar (1), said locking piece having a sleeve part through which said additional strut bar (1) runs, said braking and/or locking means having an actuator for bringing said sleeve part into frictional engagement with said additional strut bar, said actuator comprising a lever arm (3) connected at one end to said locking piece, the other end of said lever arm being subjectable to a loading force (F) for controlling the frictional engagement of said sleeve part with said additional strut bar.

2. An articulated arm system as claimed in claim 1 further including a force applying means for subjecting the other end of said lever arm to said loading force (F).

3. An articulated arm system as claimed in claim 2, characterised in that said force applying means comprises spring (4) and a solenoid (5).

4. An articulated arm system as claimed in claim 2, characterised in that said force applying means comprises a motor equipped with a self-locking worm gear.

5. An articulated arm system as claimed in claim 2, characterised in that the lever arm is operated manually.

6. An articulated arm system (20) for attaching a medical imaging device (11) to a support structure (14) in an articulated manner, the articulated arm system comprising:
   at least one parallelogram device (15a, 15b) interposable between the device and the support, said parallelogram device having at least two mutually parallel strut bars (6,7);
   a counterbalancing mechanism for said parallelogram device having at least one additional strut bar (1) and counterbalancing means (16) for holding the articulated arm system and the device (11) supported thereby in place when the device is located in a desired imaging position
   braking and/or locking means for preventing mutual linear movement of the parallel strut bars (6,7) of the parallelogram device, said braking and/or locking means having a conical locking piece (22) at least partly surrounding said additional strut bar (1), said braking and/or locking means having an actuator for pressing said conical locking piece against said additional strut bar, said actuator comprising a further conical piece (23) urged into engagement with said conical locking piece by a counterbalancing spring (16) for pressing said conical locking piece against said additional strut bar, said actuator further comprising a lever arm system (24) connected to said further conical piece (23) for urging said further conical piece out of engagement with said conical locking piece for allowing said conical locking piece to release said additional strut bar.

7. An articulated arm system as claimed in claim 6, characterised in that the conical locking piece (22) is made of an elastic material.

* * * * *